United States Patent [19]

Davis et al.

[11] Patent Number: 4,942,885

[45] Date of Patent: Jul. 24, 1990

[54] ARTICLE OF CLOTHING FOR USE AS A CONDOM

[76] Inventors: Anton Davis, 108-33, 171st Pl., Jamaica, N.Y. 11433; Kelvin A. Simmons, 15 Oakley Ave., Massapequa, N.Y. 11758; Richard Blair, 819 Hegeman Ave., Brooklyn, N.Y. 11207

[21] Appl. No.: 333,241

[22] Filed: Apr. 5, 1989

[51] Int. Cl.⁵ .............................................. A61F 13/00
[52] U.S. Cl. ..................................... 128/842; 128/844
[58] Field of Search ....................... 128/842, 843, 844; 604/347, 349, 351, 352, 353, 350

[56] References Cited

U.S. PATENT DOCUMENTS

| 1,105,488 | 7/1914 | Clare | 604/352 |
| 2,591,783 | 4/1952 | Craddock | 128/842 |
| 3,161,198 | 12/1964 | Moxley | 604/353 |
| 3,353,538 | 11/1967 | Carrigan | 604/353 |
| 3,965,900 | 6/1976 | Boedecker | 604/350 |
| 4,022,213 | 5/1977 | Stein | 604/353 |

FOREIGN PATENT DOCUMENTS 0214764 10/1984 Fed. Rep. of Germany ...... 604/353

Primary Examiner—Robert A. Hafer
Assistant Examiner—Charles H. Sam
Attorney, Agent, or Firm—Terry M. Gernstein

[57] ABSTRACT

An article of clothing prevents transmission of sexually-transmitted diseases, such as infestation of Phthirius Inguinalis to the pubic area of the wearer. The article of clothing includes a codpiece-like element that has snaps thereon for releasably attaching a condom mounting plate assembly to the codpiece-like element. A condom is held in the plate assembly.

1 Claim, 1 Drawing Sheet 4,942,885

ARTICLE OF CLOTHING FOR USE AS A CONDOM

TECHNICAL FIELD OF THE INVENTION

The present invention relates to the general art of clothing, and to the particular field of shields that are intended to protect a user against the spread of sexually transmitted diseases.

BACKGROUND OF THE INVENTION

In recent times, there have been many devices proposed for use in preventing the spread of sexually transmitted diseases. Such designs generally are directed to shielding a user's sex organ during intercourse, with the most common example of such devices being the condom.

While such organ-protecting devices have been somewhat successful in preventing the spread of certain diseases that are associated directly with contact between partner's sex organs, these devices are not fully successful in protecting against the spread of diseases, such as Phthirius Inguinalis infestation, or the like which can occur due to general contact between partners in areas adjacent to the sex organs.

However, in order to be most effective, any such device must be easily worn and provide a maximum amount of freedom. Any characteristics which are either restrictive or which make the device difficult to use will vitiate the device by discouraging its use. One of the more important aspects of the simple condom is its ease of use.

Accordingly, there is a need for a device that is as easy to use as a simple condom, yet will provide a wearer with protection against all of the diseases associated with the condom as well as those diseases that can be transmitted due to contact of the wearer and the wearer's partner in areas not generally protected by a condom.

Still further, in view of the extreme danger associated with some forms of sexually transmitted diseases, the consequences of a condom slipping or moving during use are magnified. Heretofore known condoms generally do not include any effective means for ensuring stability in use. However, such stability should not inhibit the use and/or initial placement of the condom by complicating such initial placement.

Accordingly, there is a need for an article of clothing that permits a condom to be initially placed in a manner that is quite easy, yet will still be stable and securely held in place.

OBJECTS OF THE INVENTION

It is a main object of the present invention to provide an article of clothing that serves as a sexual shield in the manner of a condom as well as in protecting the areas of the wearer's body adjacent to the areas covered by the condom.

It is another object of the present invention to provide an article of clothing that protects all of the areas of a wearer adjacent to the sex organs and still provides a large degree of freedom.

It is another object of the present invention to provide an article of clothing that permits a condom to be initially placed without any undue complications, yet will hold such condom in place without slipping or moving during use.

It is a specific object of the present invention to provide an article of clothing that can be used in the manner of a condom, yet will provide secure and stable protection to the entire pubic area.

SUMMARY OF THE INVENTION

These, and other, objects are achieved by an article of clothing that includes a codpiece-like element which covers the entire pubic area of a wearer and which includes a means for releasably fastening a condom thereto. Fastening the condom to the article of clothing ensures that the condom will remain securely in place during use, yet the initial placement of the condom is so easy as to be essentially the same as the initial placement of an unsecured condom. The article of clothing is brief enough so that freedom of movement is provided, yet the wearer is protected in the pubic area.

The wearer need only use a condom in the usual manner and still will be fully protected from diseases that attack the pubic area. In this manner, use of the device is as simple as use of the common condom, and thus such article of clothing will be used as often as a condom so that maximum protection will be afforded.

DETAILED DESCRIPTION OF THE PREFERRED EMBODIMENT OF THE INVENTION

Figure 1:
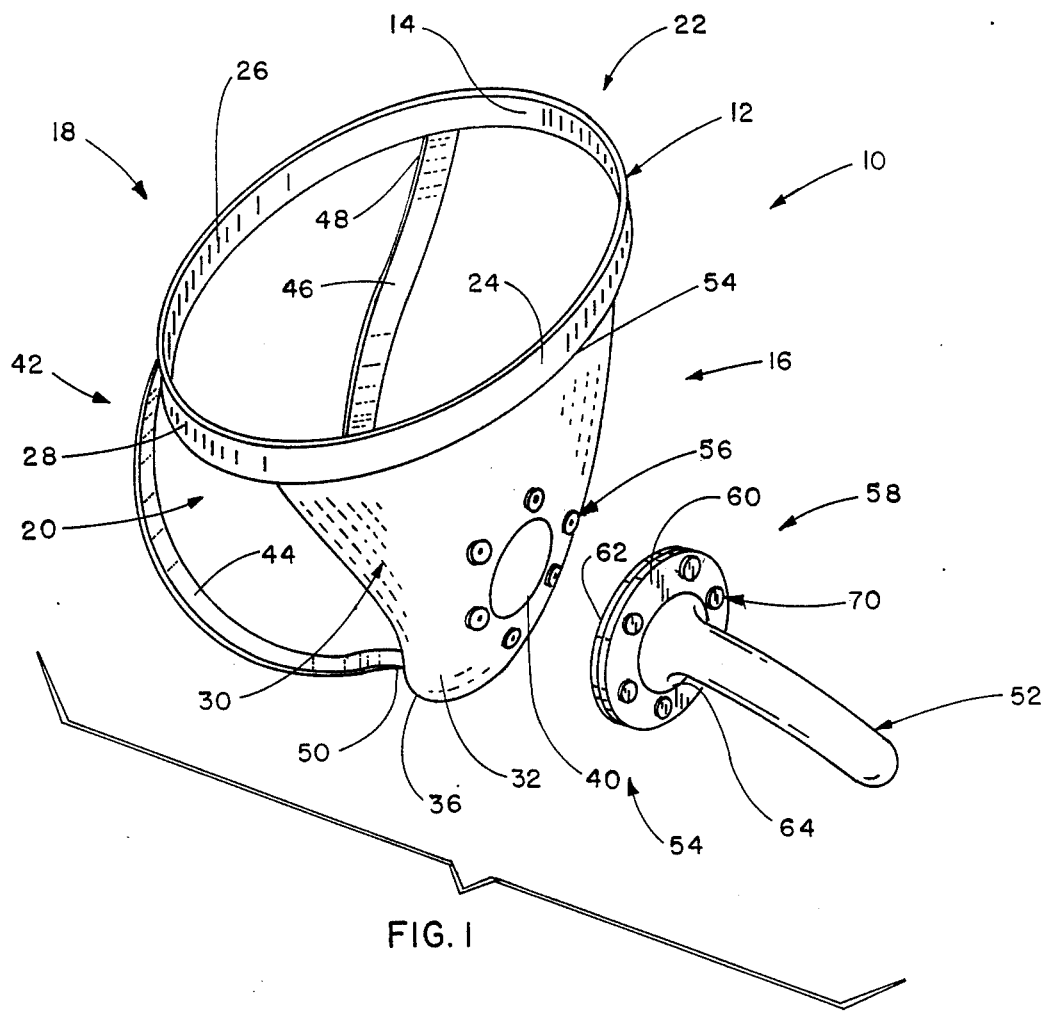
FIG. 1 is an exploded perspective showing the article of clothing embodying the present invention.

Shown in FIG. 1 is an article of clothing 10 that is intended to prevent the spread of sexually-transmitted diseases to the pubic area of the wearer as well as to the wearer via the sex organ.

The article of clothing 10 includes a monolithic body 12 that is formed of cotton or other such light fabric and which is intended to be worn in the manner of briefs. The body is monolithic to ensure its integrity, make it easier to wear and to manufacture.

The monolithic body 12 includes a waist-encircling band 14 that completely surrounds the wearer's waist when worn. In the ensuing disclosure, the various portions of the article of clothing will be described in terms that refer to the article in relation to the wearer When that article is worn. Accordingly, the article of clothing has an anterior portion 16 and a posterior portion 18 as Well as lateral portions 20 and 22.

The waist-encircling band 14 has an anterosuperior portion 24 that extends across essentially the entire frontal portion of the wearer, and a posterosuperior portion 26 that extends across essentially the entire rear area of the wearer. The waistencircling band 14 further includes two anteroposterior portions, such as portion 28 that connect the portions 24 and 26 together. The band 14 is elastic in the preferred embodiment so that one size can fit all wearers.

The article of clothing 10 further includes a codpiece-like element 30 that is sized and designed to cover essentially the entire pubic area of the wearer The element 30 is preferably made of cotton having moisture-repellant materials therein and which further includes materials and linings, such as a lining indicated at reference numeral 32, that are designed to prevent the spread of diseases associated with the pubic area, such as infestation of Phthirius Inguinalis or the like.

The element 30 thus includes a superior portion 34 fixedly and pendently attached to the anterosuperior portion 24 of the waist band 14 to depend over the wearer's pubic area in covering relation thereto.

The element 30 further includes an inferior portion 36 which is located to be positioned between the wearer's legs in use of the article of clothing 10. Locating the inferior portion 36 between the wearer's legs will ensure that the entire pubic area will be protected.

The element 30 further includes an opening 40 through which a wearer's penis is received.

The article of clothing also includes a body attaching means 42 which is located in the posterior area 18 and which includes two buttocks-encircling straps 44 and 46. Each strap is fixedly attached at a posterosuperior end 48 thereof to the posterosuperior portion 26 of the waist-encircling band 14 and at an anteroinferior end 50 thereof to the inferior portion 36 of the codpiece-like element 30. The straps 44 and 46 also are formed of elastic-type material so that a single size will universally fit all wearers.

The article of clothing 10 is adapted for use in conjunction with a condom, such as condom 52, and thus has means 54 for attaching such condom to the codpiece-like element 30 adjacent to the wearer's penis. The attaching means 54 is designed to be easily and quickly actuated and to securely hold the condom in place. The quick actuation of the attaching means permits the article of clothing 10 to be used in as easy and as expeditious a manner as a simple condom.

Figure 2:
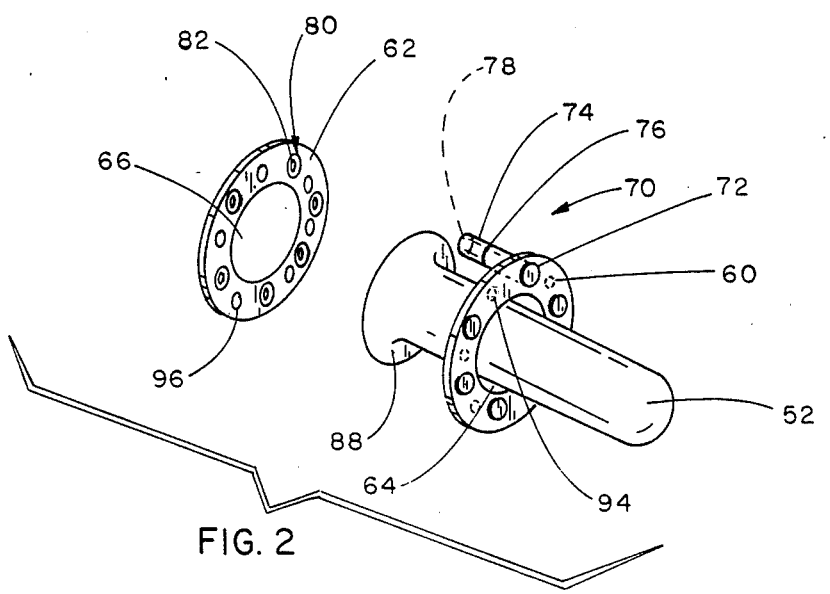
FIG. 2 is an exploded perspective showing the means for attaching a condom to the article of clothing shown in FIG. 1.

As shown in FIGS. 1 and 2, the attaching means includes a plurality of fasteners, such as snap 56, mounted on the codpiecelike element 30 in an angularly spaced apart manner and in circumambient relationship to the opening 40. The snap elements 56 are similar to the general snaps found on clothing, and are mounted accordingly.

The attaching means further includes an annular condom mounting plate assembly 58 that is adapted to releasably hold the condom in covering relation over the opening 40. The mounting plate assembly 58 includes two concentrically arranged plate elements 60 and 62, having openings 64 and 66 respectively that are arranged to be concentric with the opening 40 when the attaching means is in use.

The attaching means 54 further includes snap-fastener receiving elements 70 which releasably attach the plate assembly to the element 30 via the snaps 56. The elements 70 are in angularly spaced relationship about the mounting plate assembly 58. The snap-fastener receiving elements are shown in FIG. 1, and one of such elements 70 is shown in FIG. 2 in its complete form. The element 70 shown in FIG. 2 is not to scale so that all of the various parts thereof can be clearly illustrated, and the remaining elements are not shown in FIG. 2 for the sake of clarity. However, no limitation is intended by such showing.

Each snap-fastener receiving element includes a base 72 fixedly mounted at its proximal end on the plate 60, and an elongate body 74 extending therefrom. The body 74 includes a groove 76 defined therein for releasably attaching the element to the plate 62 as will be discussed below. The groove 76 is located on the body 74 so that the plates 60 and 62 are held in abutting relationship as shown in FIG. 1 when the groove 76 is used to attach the plate 60 to the plate 62 via the element 70.

The body 74 further includes a blind-ended bore 78 defined in its distal end. The bore 78 is sized to snappingly receive and hold an associated snap of the snaps 56 to snappingly attach the plate assembly 58 to the codpiece-like element 30.

The plate 62 includes a plurality of openings 80 defined at angularly spaced locations about the opening 66 thereof to accommodate the bodies 74 therethrough. Each opening 80 includes a projection 82 which is flexible, yet strong, and which is received in groove 76 on the body 70 accommodated therein to snappingly fix the plate 62 to the plate 60 via the bodies 70. The grooves 76 and the projections 82 co-operate to form a mounting plate assembly coupling means.

As is best shown in FIG. 2, the condom 52 includes a base 88. This base is trapped between the plates 60 and 62 and the plates are forced together to engage the projections 82 in the grooves 76 to couple the plates together. Alternatively, as shown in FIG. 2, the condom base can be securely held in place by means such as one or more projections 94 on plate element 60 that co-operate with one or more depressions 96 on the plate element 62. The projections will force portions of the base material 88 into the associated depressions to mechanically hold the condom in place when the plate elements are coupled together. The condom will be securely held in position by such abutting engagement, yet such secure mounting of the condom will not substantially interfere with the initial placement of the condom. The condom will thus be releasably held in position on the plate assembly. Such releasable mounting will permit the condom to be discarded after use, and another condom can replace the discarded condom. In this manner, the article of clothing 10 can be used in conjunction With condoms as are presently available.

The condom base material can also be permanently affixed to the plate assembly and the entire assembly, including a condom and the plates, sold as a single unit in the manner of a condom. For example, the condom base material can be affixed to the plate assembly by glue, sonic sealing, heat sealing or like means, or the above-described mechanical coupling of the plate elements together and the mechanical coupling of the condom to the plate elements can be made permanent by using one-way elements or the like.

The above-described co-operation of the elements of the mounting plate assembly function as a condom mounting means for mounting a condom on the mounting plate assembly either releasably or permanently.

The plate assembly 58 is preferably made of flexible plastics-like material, and can be sold as a unit with the condom whereby the entire unit can be removed from a package and snapped into place on the codpiece-like element 30 in the manner common to condoms whereby the entire article of clothing is used in a manner not substantially different from the usual condom use process. If the releasable mounting mode is used, the entire unit need be purchased only once, and thereafter the usual condom is purchased and substituted for the condom being discarded.

It is to be understood that while certain forms of the present invention have been illustrated and described herein, it is not to be limited to the specific forms or arrangement of parts described and shown.

We claim:
1. An article of clothing for preventing transmission of sexually-related diseases comprising:
   (A) a monolithic body portion which includes

(1) a waist-encircling band having an anterosuperior portion, a posterosuperior portion and an anteroposterior portion when worn by a user,
(2) a codpiece-like element including
   (a) a superior portion pendently attached to said waist-encircling band anterosuperior portion,
   (b) an inferior portion,
   (c) said codpiece-like element being sized and shaped to cover essentially the entire pubic area of a user and to have said inferior portion thereof located between the user's leges when worn and having an opening positioned thererin to receive a user's penis therethrough,
(3) two buttocks encircling straps each attached at one end to said band posterosuperior portion and at the other end to said codpiece-like element inferior portion to extend posterioranteriorly between the user's legs when worn; and
(B) condom-attaching means which includes
(1) a flexible plastic annular mounting plate assembly sized to surround said codpiece-like element opening,
(2) mounting plate fastener means on said codpiece-like element, said mounting plate fastener means including a plurality of angularly spaced apart snaps located circumjacent to said codpiece-like element opening,
(3) fastener receiving means on said mounting plate assembly for co-operating with said mounting plate fastener means to releasably secure said mounting plate assembly to said codpiece-like element, said fastener receiving means including a plurality of angularly spaced apart snap receiving elements,
(4) condom mounting means on said mounting plate assembly for mounting a condom on said mounting plate assembly in a position to cover said codpiece-like element opening, said condom attaching means mounting plate assembly including two concentric annular plate elements,
(5) one annular plate element of said two concentric annular plate elements including a plurality of openings defined therethrough,
(6) mounting plate coupling means for releasably coupling said two concentric annular plate elements together, said mounting plate coupling means being positioned adjacent to said snap fasteners on said codpiece-like element, and including
(a) a plurality of projecting snap fastener-receiving elements mounted on the other condom mounting means annular plate element in position to be received through said angularly spaced apart openings in said one annular plate element,
(b) each projecting snap fastener-receiving element including
   (1) an elongated body,
   (2) a base located at a proximal end of said body and which is fixedly mounted on the other annular plate element,
   (3) said elongated body extending through said other annular plate element,
   (4) a groove defined in said elongated body, and
   (5) a blind-ended bore defined in a distal end of said elongated body, said blind-ended bore being sized and shaped to snappingly receive one of said angularly spaced apart snaps mounted on said codpiece-like element to releasably couple said other annular plate element to said codpiece-like element with said one annular plate element trapped between said codpiece-like element and said other annular plate element,
(c) a projection mounted on said one annular plate element to extend into each of said angularly spaced apart openings, each of said projections being flexible and sized to engage into a groove of a snap fastener-receiving element to snappingly lock said body to said one annular plate element,
(d) a plurality of dimple-like projections on said other annular plate element, and
(e) a plurality of dimple-like depressions defined in said one annular plate element in position to receive a one dimple-like projection in each dimple-like depression and capture a condom between said dimple-like projection and said one annular plate element.

* * * * *